United States Patent
Cerni et al.

(10) Patent No.: US 6,246,474 B1
(45) Date of Patent: *Jun. 12, 2001

(54) METHOD AND APPARATUS FOR MEASUREMENT OF PARTICLE SIZE DISTRIBUTION IN SUBSTANTIALLY OPAQUE SLURRIES

(75) Inventors: Todd A. Cerni, Longmont; Scott Waisanen, Louisville, both of CO (US)

(73) Assignee: Particle Measuring Systems, Inc., Boulder, CO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/069,682

(22) Filed: Apr. 29, 1998

(51) Int. Cl.[7] .................................... G01N 15/02
(52) U.S. Cl. ........................... 356/335; 356/246; 438/16
(58) Field of Search .................... 356/335, 336, 356/337, 338, 339, 340, 341, 342, 343, 244, 246, 440; 73/61.71, 61.73; 438/692, 693, 7, 8, 16, 747; 216/85

(56) References Cited

U.S. PATENT DOCUMENTS

| | | | |
|---|---|---|---|
| 4,071,298 | * | 1/1978 | Falconer .............................. 356/336 |
| 4,279,512 | | 7/1981 | Tunstall ............................... 356/335 |
| 4,318,180 | | 3/1982 | Lundqvist et al. .................. 364/555 |

(List continued on next page.)

FOREIGN PATENT DOCUMENTS

| | | |
|---|---|---|
| 0 564 157 A1 | 6/1993 | (EP) . |
| 0 590 841 A1 | 6/1994 | (EP) . |
| 0 654 661 A1 | 5/1995 | (EP) . |
| 2 424 102 | 7/1980 | (FR) . |

OTHER PUBLICATIONS

S. Twomey; "Comparison of Constrained Linear Inversion and an Iterative Nonlinear Algorithm Applied to the Indirect Estimation of Particle Size Distributions"; received Jun. 6, 1974, revision Feb. 18, 1975; *Journal of Computational Physics*, vol. 18, No. 2, Jun. 1975.

Theodora Kourti and John F. MacGregor; "Particle Size Determination Using Turbidimetry—Capabilities, Limitations, and Evaluation for On–Line Applications"; received May 14, 1991; Chapter 3, *Particle Size Distribution II*, American Chemical Society, 1991 (0097–6156/91/0472–0034$0.850/0).

"Commercial spectrophotomer for particle sizing", Fabio Ferri, Alessandra Bassini, and Enrico Paganini, *Applied Optics*, Feb. 1, 1997, vol. 36, No. 4, pp. 885–891.

(List continued on next page.)

*Primary Examiner*—Hao Q. Pham
(74) *Attorney, Agent, or Firm*—Duft, Graziano & Forest, P.C.

(57) ABSTRACT

A very sensitive particle distribution probe uses special processing including a modified Twomey/Chahine iterative convergence technique and a specially constructed sample cell to obtain particle size distribution measurements from optically dense slurries, such as the slurries used in the semiconductor industry for chemical mechanical planarization. Spectral transmission data is taken over the spectral range of 0.20–2.5 microns, utilizing specially constructed, chemically resistant sample cells of 50–250 microns thickness, and miniature, fixed grating, linear detector array spectrometers. At wavelengths greater than 1 micron, the preferred design utilizes InGaAs linear detector arrays. An ultrasonic disrupter can be employed to breakup harmless soft agglomerates. In addition to direct particle size distribution measurement, the invention described here could be used to detect other fundamental causes of slurry degradation, such as foaming and jelling. The probe accomplishes continuous, real time sampling of undiluted slurry. A three-position chopper allows automated operation in an industrial environment without the need for frequent reference spectra, which would require taking the probe off-line.

48 Claims, 7 Drawing Sheets

U.S. PATENT DOCUMENTS

| | | | | |
|---|---|---|---|---|
| 4,329,053 | * | 5/1982 | Fymat | 356/336 |
| 4,338,030 | | 7/1982 | Loos | 356/336 |
| 4,652,755 | | 3/1987 | Solomon et al. | 250/341 |
| 4,790,652 | | 12/1988 | Unéus et al. | 356/45 |
| 5,007,297 | | 4/1991 | Sommer | 73/865.5 |
| 5,164,787 | * | 11/1992 | Igushi et al. | 356/336 |
| 5,371,020 | * | 12/1994 | Frischauf | 356/246 |
| 5,475,486 | | 12/1995 | Paoli | 356/246 |
| 5,485,270 | | 1/1996 | Freud et al. | 356/336 |
| 5,561,520 | * | 10/1996 | Williams | 356/335 |
| 5,616,457 | | 4/1997 | García-Rubio | 435/4 |
| 5,710,069 | | 1/1998 | Farkas et al. | 438/7 |
| 5,790,246 | * | 8/1998 | Kuhnell et al. | 356/72 |
| 5,940,177 | * | 8/1999 | Esser et al. | 356/338 |

OTHER PUBLICATIONS

"Analysis of particle sizes, concentration, and refractive index in measurement of light transmittance in the forward–scattering–angle range", Anatoil P. Nefedov, Oleg F. Petrov, and Olga S. Vaulina, *Applied Optics*, Feb. 20, 1997, vol. 36, No. 6, pp. 1357–1366.

International Search Report, Jul. 28, 1999, European Patent Office, P.B. 5818 Patentlaan 2, NL–2280 HV Rijswijk.

* cited by examiner

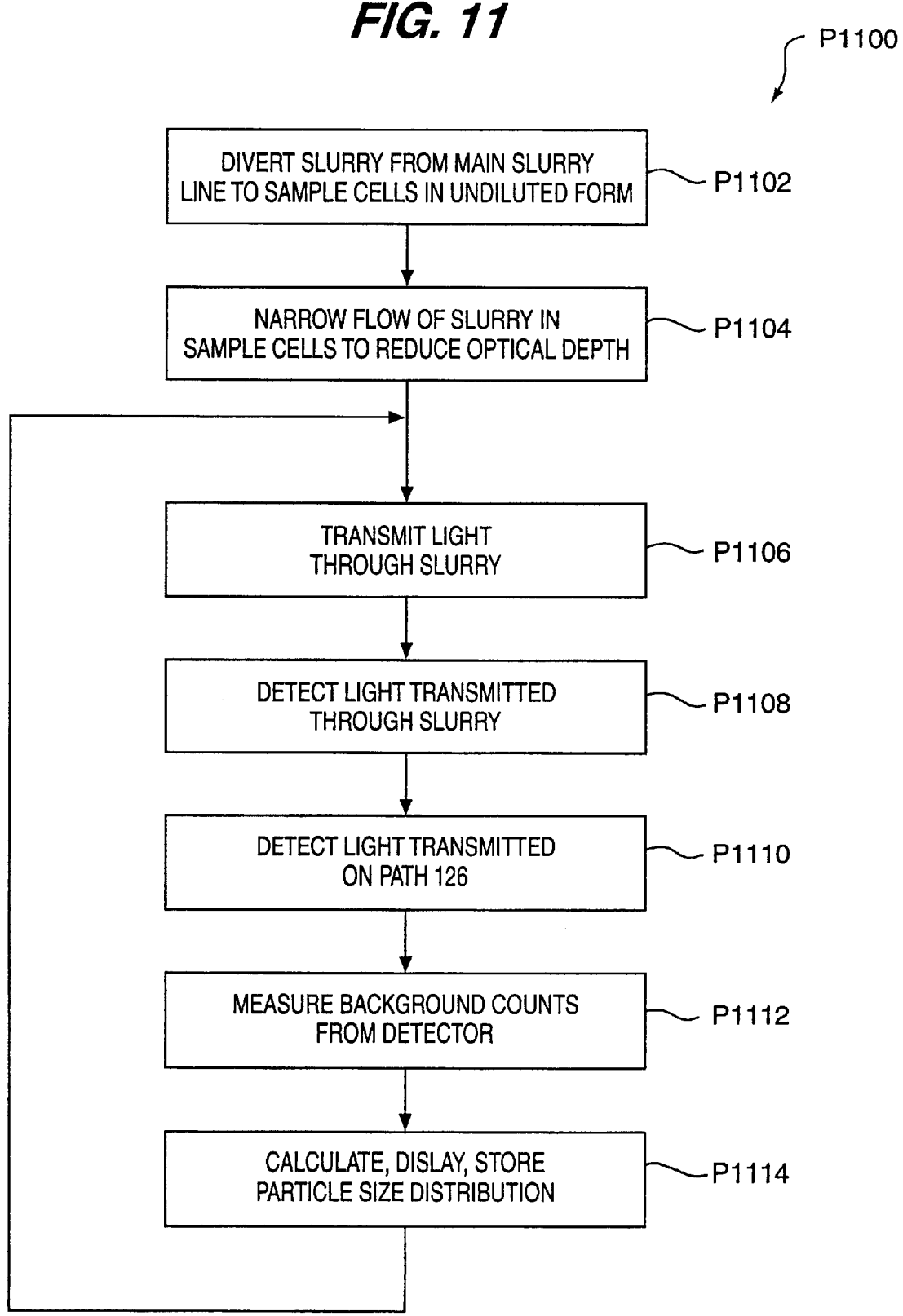

METHOD AND APPARATUS FOR MEASUREMENT OF PARTICLE SIZE DISTRIBUTION IN SUBSTANTIALLY OPAQUE SLURRIES

BACKGROUND OF THE INVENTION

1. Field of the Invention

The present invention pertains to the field of measurements performed on slurries to determine the slurry particle size distribution. More specifically, the measurements concern a use of instrumentation to determine the particle concentration as a function of size in substantially opaque slurries, such as the chemical mechanical planarization ("CMP") slurries that are currently used in semiconductor manufacturing.

2. Statement of the Problem

CMP processes are used in the semiconductor and optics industries to provide ultrasmooth surfaces. CMP slurries for use in these processes typically consist of $SiO_2$ or $Al_2O_3$ particles suspended in an acid or base solution to a concentration of 4% to 18% solids by weight. The $SiO_2$ slurries are referred to in the art as 'oxide' slurries, and the $Al_2O_3$ slurries are referred to as 'metal' slurries. It is difficult to check the quality of particle size distribution due to the submicron sizes of the particles and the substantially opaque nature of CMP slurries.

CMP slurries are used to facilitate the deposition of uniform planarized layers in multiple layer wafers. The use of CMP slurry results is ultrasmooth surfaces that enhance the resolution of embedded microfeatures in integrated circuits. Particles having dimensions that exceed a delimiting value for a particular application are analogous to sandpaper having grit that is too large, and disadvantageously score or scratch the surface that is being smoothed. Thus, it is an essential quality control operation to eliminate the use of slurries having particles that are too large.

The use of CMP slurries in semiconductor manufacturing has risen sharply over the last 5 years. It has emerged as the preferred method of planarization for manufacture of multiple layer semiconductor wafers having feature sizes less than or equal to 0.35 micron. It has been observed that semiconductor wafers can be scratched and thereby damaged if a significant concentration of large particles appear in the slurry through either contamination or agglomeration. The size threshold for particles that are large enough to damage wafers is a process dependent value that still poorly known, but is believed to be in the range of 0.5–3.0 microns. CMP slurry manufacturers attempt to produce slurries that consist predominantly of particles less than 0.5 micron in size.

Commercially available sensor devices are presently unable to meet the needs of those who wish to measure the particle size distribution of CMP slurries. It is desirable to perform continuous measurements of the CMP slurry particle size distribution in real time, in order to eliminate the risk of using slurries having particles or agglomerated particles that are too large. This enhanced process control, if available, would allow early detection and cure of slurry problems. The use of the term "real time" in this discussion means that the measurement results are available within a few seconds after sampling. It is also desirable to measure the particle size distribution of undiluted slurry because dilution and the subsequent change in pH can alter the distribution. Furthermore, dilution combined with continuous sampling creates large volumes of waste slurry. These needs characterize the present state of the art in measuring the particle size distribution of CMP slurries.

Existing commercial particle size sensors include those based on measurement of angular light scattering, dynamic light scattering or photon correlation spectroscopy, ultrasonic transmission, and capillary hydrodynamic fractionalization. These measurement techniques are problematic because they require substantial dilution of the optically dense CMP slurries, discontinuous batch sampling of the slurry, or have insufficient sensitivity to detect small changes in the particle size distribution over the critical size range of 0.5 to 3.0 microns.

The need to dilute CMP slurries for particle size measurements creates large amounts of waste that cannot be reinjected back into the CMP slurry. According to the data of Bare and Lemke: "Monitoring slurry stability to reduce process variability", Micro. Vol. 15, No. 8, pp. 53–63 (1997), oxide slurries typically have $2 \times 10^5/cm^3$ particles greater than one micron, and metal slurries typically have $7 \times 10^8/cm^3$ particles greater than one micron. This data was obtained using a Particle Measurement Systems LiQuilaz SO5 particle size detector, which is specified for a maximum particle concentration of $12,000/cm^3$ to keep coincidence errors less than ten percent. The SO5 detector is typical of commercially available single particle light scattering devices. Thus, a minimum dilution factor of 17 is required to reduce coincidence errors for oxide slurries, and a minimum dilution factor of 58,350 is required for metal slurries. These dilution factors represent significant amounts of process slurry waste, and the dilution itself is suspected of altering the size distribution through agglomeration.

U.S. Pat. No. 5,710,069 to Farkas et al. discusses an optical particle counter that detects only one particle at a time in CMP slurries. The single particle must flow through a sample volume consisting of the intersection of a light beam and a detector field of view. The '069 patent does not discuss the difficulty in requiring the light beam to penetrate the slurry towards the measurement area (sample volume), nor in achieving detection of one particle at a time in slurries which typically contain of $10^{13}$–$10^{14}$ particles per $cm^3$. The idea of being able to measure only one particle at a time is unsupported by any calculations, numerical arguments, or design details. It is unclear whether the '069 patent uses Mie scattering calculations or empirical correlations to calculate a particle size distribution based upon the number of single particles that are counted. The technique of "photocorrelation" is said not to work, but no description is provided of a technique that does work. U.S. Pat. No. 5,616,457 to Garcia-Rubio teaches an apparatus for detecting the presence of a microorganism in a sample of liquid. A Twomey linear inversion with a smoothing constraint is used to calculate a particle size distribution for the organism. A standard commercial spectrophotometer having a one cm cell path length is used to perform the measurements. Additional detail regarding the Twomey linear inversion can be found in Twomey, "Comparison of constrained linear inversion and an iterative nonlinear algorithm applied to the indirect estimation of particle size distributions", J. Comp. Phys. Vol. 18, No. 2, 188–200 (1975). The '457 patent does not require dilution because it addresses solutions that are much less optically dense than CMP slurries.

Examples of the present state of the art in measuring particle size distribution in optically dense mixtures of submicron particles suspended in a liquid solution include two presentations at a recent American Chemical Society symposium, namely, Kourti and MacGregor, "Particle size determination using turbidimetry", Particle Size Distribution II—Assessment and Characterization, pp. 35–63, Amer. Chem. Soc. Symposium No. 472 (1991); and Brandolin and Garcia-Rubio, "On-line partide size distribution measurements for latex reactors", Particle Size Distribution II—Assessment and Characterization, pp. 65–85 (1991). These authors typically utilize measurements at 2–3 wavelengths in the range of 0.2–1.0 microns. Conventional sample cells on the order of 1.0 cm in thickness were apparently utilized. The limited wavelength range and conventional sample cell dimensions force significant sample dilution, which in turn results in generation of a large waste stream of diluted product. An off-line batch sampling system may also be used, but this type of system has an unacceptably slow time response.

There remains a need for a real-time probe for use in obtaining continuous particle size distribution measurements that do not require dilution of the CMP slurry. The probe must retrieve the particle distribution over a broad range of sizes, and be capable of consistently detecting small changes in the size distribution, while providing autonomous operation in an industrial environment.

SOLUTION

The present invention overcomes the problems that are outlined above, and advances the art by providing a real-time apparatus for continuous particle size distribution measurements of undiluted CMP slurry over a broad range of sizes, with high sensitivity to small changes in the size distribution and with autonomous operation in a industrial environment. These advantages are obtained by measuring spectral transmission through an undiluted sample of the slurry at many wavelengths over a broad wavelength range, with a novel sensor design. These spectral transmission measurements are made possible by using one or more flow through sample cells having widths as narrow as 50 microns. CMP slurries have very high optical extinction per unit length in the visible spectrum by virtue of the very high particle concentration and submicron sizes. A reasonable fraction of the incident light beam, i.e., an amount greater than approximately 5%, must penetrate the sample without being scattered, in order to obtain useful spectral transmission data. This goal is accomplished by extending the spectral transmission measurements to 2.5 microns in wavelength, which is well beyond the 1.0 micron limit used in past work, and utilizing specially constructed sample cells having a path length of 50–250 microns in thickness. A spectral wavelength range of 0.20–2.5 microns is used to retrieve the entire CMP slurry particle size distribution for the full range of CMP slurries that are currently used in semiconductor manufacturing.

A particle size distribution probe according to the invention is used for measuring the particle size distribution of optically dense slurries with undiluted, continuous, on-line sampling for real time process control. The probe includes a plurality of light sources, a detector system which may be comprised of a plurality of fixed grating linear detector array spectrometers, a plurality of sample cells, a three position chopper, and an optical pathway for transmitting light from the light sources through the sample cells and then to the detector system or spectrometers. A computer or microprocessor receives detector signals, and performs a particle size distribution measurement. The sample cells are specially constructed to reduce optical depth in the slurry, which permits particle size distribution measurements without dilution of the slurry.

Optical depth is the dimensionless extinction parameter in the exponential transmission function (Beer's law), and is defined as the product of an extinction per unit length in the slurry times a thickness of the slurry in an optical path through the sample cell. Optically dense slurry is hereby defined as a particulate polydispersion consisting of 1–30% solids by weight of submicron particles, suspended in a liquid. CMP slurries are optically dense slurries that typically exhibit an optical depth of greater than 10, at 0.5 microns wavelength in a conventional sample cell having a one centimeter path length, thus yielding a transmission of less than 0.00005. As stated above, the reduction in optical depth derives from a substantial narrowing of the conventional flow path length in the sample cell to a length ranging from 50 to 250 microns.

The sample cells are formed of a chemically resistant housing that retains first window and a second window in spaced relationship to provide a suitable optical depth. These windows are preferably made of a very hard, chemically resistant, artificial crystal, such as sapphire. The housing includes a tapered ramp that widens as it narrows from an inlet to the separation between the windows, and thins as it thickens from the separation to an outlet. The outlet preferably returns undiluted slurry to the day tank or main process slurry line after particle size distribution measurements have been obtained from the sample. The use of multiple sample cells yields measurements of greater accuracy by tuning the optical path length (window spacing) of each cell to a different wavelength regime. Specifically, greater accuracy measurements can be obtained by keeping the transmission, measured through the slurry, within the approximate range of 0.10–0.90.

A light chopper is positioned between the light source and the sample cell. The chopper contains a plurality of holes for transmitting light to the sample cell and a plurality of mirrors or solid regions means for blocking transmission of light to the sample cell. The mirrors allow measurement of the time and temperature drift of the sources, while the solid region allows measurement of the time and temperature drift of the spectrometers and their detectors. These features allow autonomous operation in an industrial environment and eliminate the need for frequent measurement of reference spectra, which would require taking the probe off-line. The computer or microprocessor preferably uses a modified Twomey/Chahine-based nonlinear iterative conversion to calculate a particle size distribution measurement from the spectral transmission measurements. A plurality of fixed grating spectrometers each having a detector array are used to assist in this calculation. An ultrasonic disrupter may be used to disrupt soft slurry agglomerations just prior to their entry into the ample cell.

The probe is operated continuously and in real time by diverting a portion of optically dense slurry from a main slurry line, introducing the slurry into a sample cell in undiluted form, narrowing flow of the optically dense slurry within the sample cell to reduce optical depth in the slurry, transmitting light through the slurry, detecting light transmitted through the slurry in the sample cell with production of corresponding detector signals, and calculating a particle size distribution through use of the detector signals.

BRIEF DESCRIPTION OF THE DRAWINGS

FIG. 11 depicts a schematic process diagram for use in operating the probe shown in FIG. 1.

DETAILED DESCRIPTION OF THE PREFERRED EMBODIMENT

Figure 1:
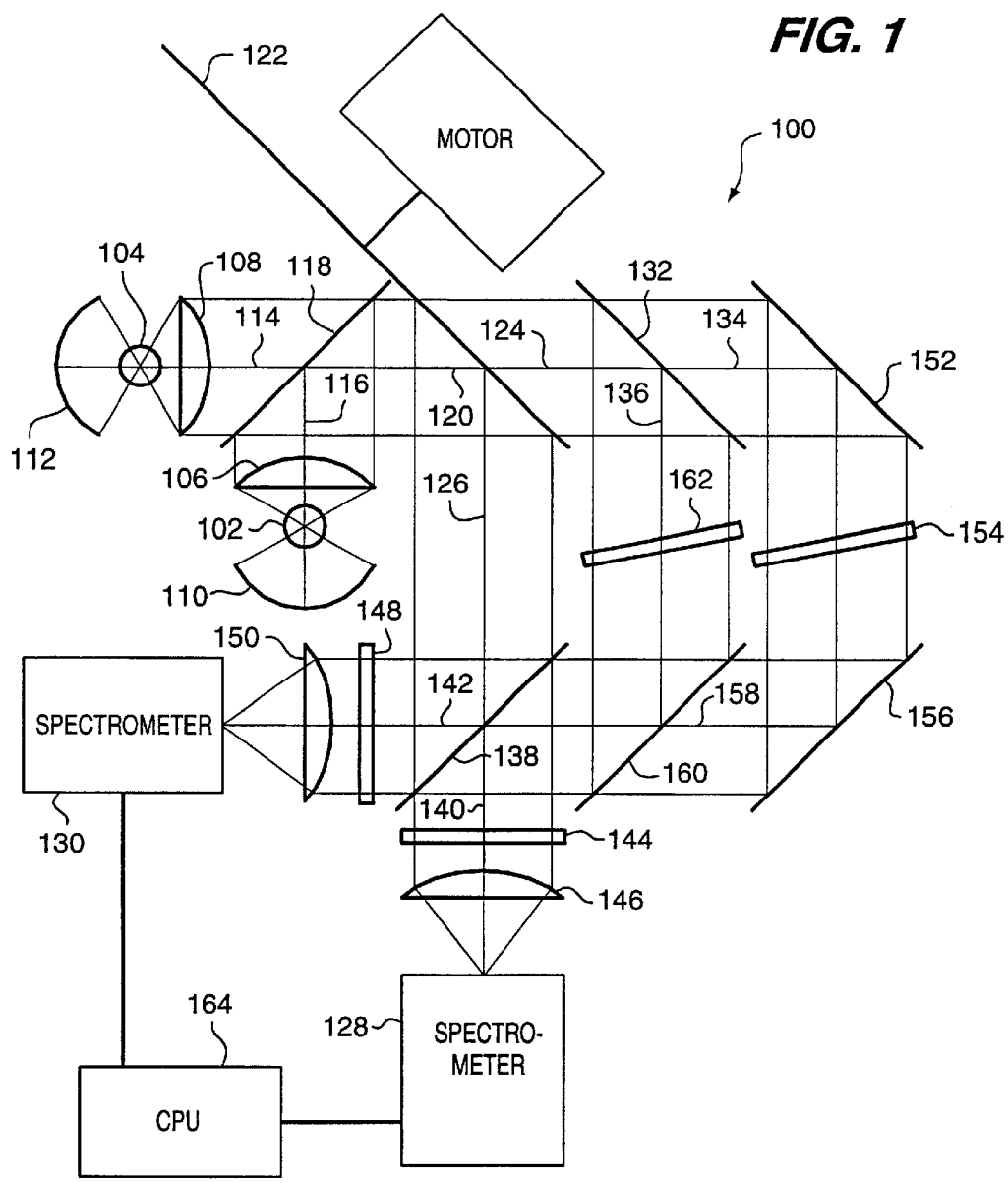
FIG. 1 depicts a sample of a probe for use in measuring particle size distributions according to the invention.

FIG. 1 is an optical system schematic of a CMP slurry particle size distribution probe 100. A deuterium source 102 supplies ultraviolet radiation, while a quartz tungsten halogen source 104 supplies visible and infrared radiation. The light from each of sources 102 and 104 is collimated by a combination of a corresponding lens 106 and 108, and a corresponding a mirror 110 and 112, which provide respective collimated beams 114 and 116. A long pass filter 118 combines the two collimated beams 114 and 116 into a single collimated beam 120.

Figure 2:
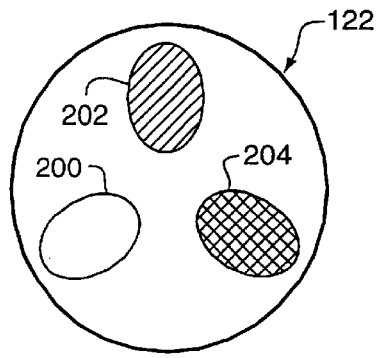
FIG. 2 depicts a light chopper blade for use in the probe of FIG. 1.

A motor-driven rotational chopper blade 122 intersects the combined collimated beam 120, and provides three different measurements in quick succession. As shown in FIG. 2, chopper blade 122 contains three ellipsoid features, namely, hole 200, mirror 202, and solid, nonreflective disk 204. Hole 200 permits transmission of light through chopper blade 122 for passage of collimated beam 120 onto pathway 124 (see FIG. 1). Mirror 202 allows measurement of source irradiance, which drifts with temperature and time, by reflecting light onto pathway 126. The solid disk 204 allows measurement of the electronic offsets by preventing light from reaching the charge coupled device detector arrays within two miniature, fixed grating, linear detector array spectrometers 128 and 130. These electronic offsets are a substantial source of error for the detector arrays if uncorrected, and the offsets drift with temperature and time.

Use of the mechanical chopper 122 permits real time calibration of probe 100 interspersed with actual measurement data, as facilitated by the respective optical pathways that are described below. Use of the mechanical chopper 122 also allows signal-to-noise enhancement that is associated with lock-in detection and signal processing techniques.

Light passing through hole 200 of chopper blade 122 travels on pathway 124 towards a long pass filter 132, which is used as a beam splitter. For oxide CMP slurries, long wavelengths greater than about 0.55 microns pass through the long pass filter 132 onto pathway 134 while shorter wavelengths are reflected onto pathway 136. For metal CMP slurries, the long pass filter will accomplish wavelength division at approximately 1.0 to 1.25 micron.

Light that is reflected from chopper blade 122 by mirror 202 travels along path 126 towards a 50/50 beam splitter 138 for splitting of the light on pathway 126 into two beams 140 and 142 of equal intensity. Beam 140 travels through an order sorting or blocking filter 144 and gathering lens 146 towards the fixed grating spectrophotometer 128. Beam 142 travels through an order sorting or blocking filter 148 and gathering lens 150 towards the fixed grating spectrophotometer 130.

The order sorting filters 144 and 148 are required because any grating will create higher orders of the fundamental wavelength. It is anticipated that the wavelength coverage of the two spectrometers 128 and 130 will be approximately be 0.20 to 0.50 microns and 0.50 to 1.0 microns respectively for oxide CMP slurries, and 0.5 to 1.0 microns and 1.25 to 2.5 microns respectively for metal CMP slurries. Spectrometers operating at wavelengths shorter than 1.0 micron will utilize Si detector arrays, and those operating at longer wavelengths will utilize InGaAs detector arrays.

Light passing through long pass filter 132 onto pathway 134 is directed towards a first mirror 152 for reflection through a first sample cell 154. Light that has been transmitted through first sample cell 154 is reflected by a second mirror 156 along pathway 158 through long pass filter 160. Long pass filter 160 is preferably identical to long pass filter 132, and both filters may be changed to provide appropriate instrument sensitivity in the intended environment of use. Light on pathway 158 passes through long pass filter 160, and is eventually split 50/50 by beam splitter 138 for delivery to spectrophotometers 128 and 130.

Light reflected by long pass filter 132 onto pathway 136 travels through a second sample cell 162. Light that has been transmitted through the second sample cell 162 is reflected by long pass filter 160 towards 50/50 beam splitter 138 for delivery of light to spectrophotometers 128 and 130. The use of multiple sample cells yields measurements of greater accuracy by tuning the optical path length (window spacing) of each cell to a different wavelength regime. Tuning is accomplished by maintaining transmission through the cells in a range between about 0.10 to 0.90.

The spectrometers 128 and 130 are collectively referred to herein as a detector or detector group. Each spectrometer preferably includes an internal fixed grating to enhance speed of measurement and reliability, i.e.; the preferred spectrometers are not scanning spectrometers having a movable grating. The internal fixed grating is configured to place dispersed light having selected wavelengths on an internal array of conventional detector elements concealed within each spectrometer. Thus, each spectrometer is operable to detect a range of wavelengths. A computer 164 receives signals from the detector group including spectrophotometers 128 and 130, and uses these signals to calculate a particle size distribution corresponding to the CMP slurry being measured.

In embodiments where the slurry is not optically dense, the sample cells 154 and 162 may be removed to provide an open pathway adapted to receive a pharmaceutical mist, such as a mist from a medical nebulizer for delivery of medication to asthmatics. The sample cells may also be replaced by an open tube or chamber. In this manner, the probe can be used to measure the particle size distribution of aerosol mists.

Specially Constructed Sample Cells Reduce Optical Depth

Figure 3:
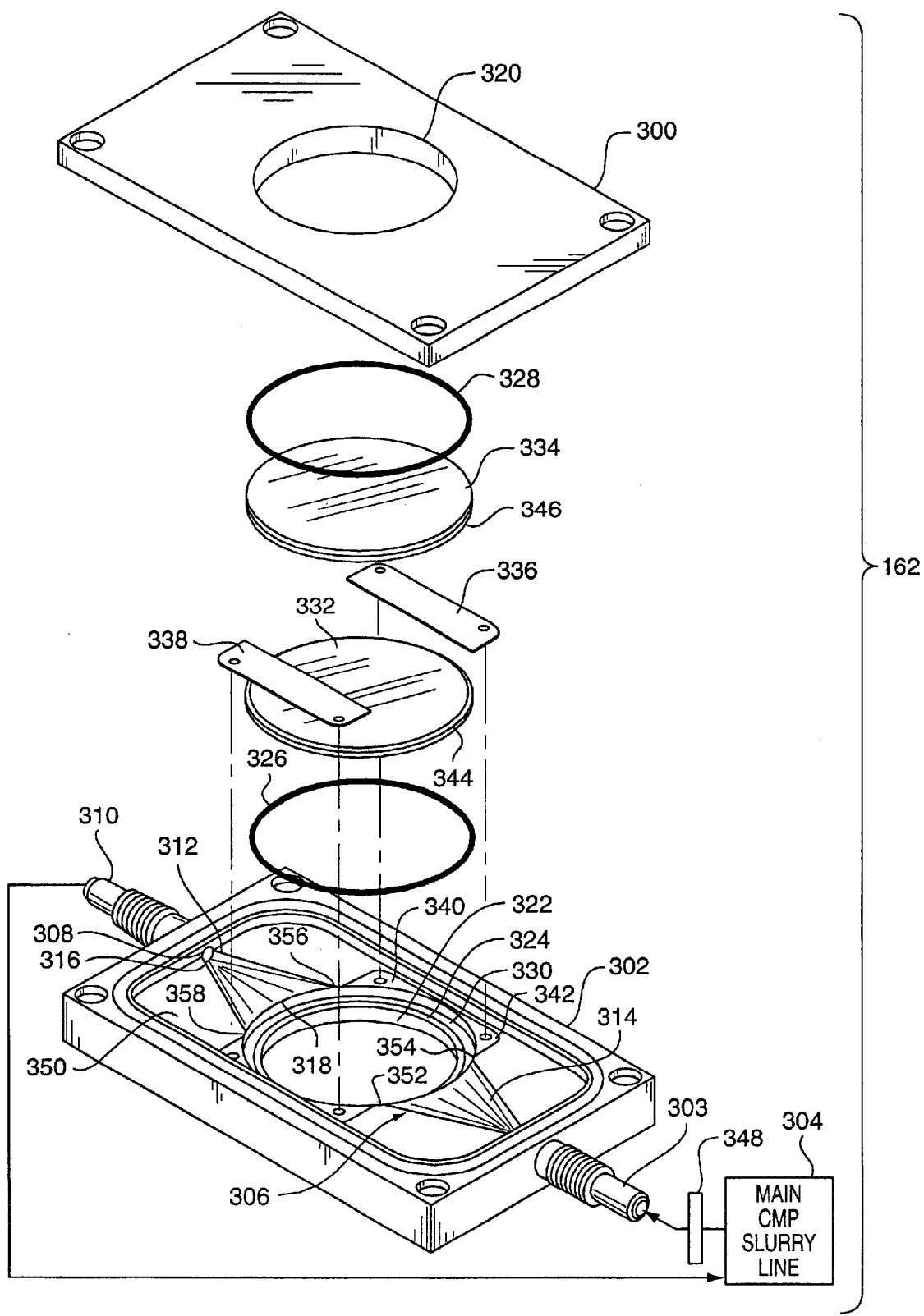
FIG. 3 depicts a first specially constructed sample cell for use in the probe of FIG. 1.

FIG. 3 gives a detailed assembly view of a preferred CMP slurry sample cell 162 (see FIG. 1), which is intended for use with optically dense slurries. Both cells 154 and 162 share the same basic features, but the depth of the cells may be selectively adjusted to accommodate the increasing transmissivity of longer wavelength radiation in cell 154 (see FIG. 1).

A housing is formed of top plate 300 and bottom plate 302, which are each machined from a solid block of chemically resistant material such as Kel-F, polyvinyldifluoride ("PVDF") or polyvinyldichloride ("PVDC"). Sample cell inlet line 303 is connected with an inlet port (not depicted) through which the undiluted CMP slurry from main CMP slurry line 304 enters the interior space 306 of sample cell 162. Outlet port 308 drains the slurry from space 306 into outlet line 310. Each of top plate 300 and bottom plate 302 are provided with an opposed pair of triangular tapered ramps, e.g., ramps 312 and 314. These ramps are thickest at their respective tips proximate the corresponding port, e.g., tip 316 proximate outlet port 308, and which widen and narrow towards a base remote from the port, e.g., base 318.

Each of top and bottom plates 300 and 302 are respectively provided with centrally located circular apertures 320 and 322. The interior portions of plates 300 and 302 contain a groove 324, for receipt of corresponding elastomeric O-rings 326 and 328. A bevel 330 receives sapphire windows 332 and 334. A pair of opposed spacers 336 and 338 are retained against flow by corresponding retaining pins, e.g., retaining pins 340 and 342, and fit between sapphire windows 332 and 334.

The sapphire windows 332 and 334 and opposed spacers 336 and 338 define the optical viewing area available to path 136 (see FIG. 1). The optical viewing area preferably ranges between 50 and 250 microns in thickness between windows 332 and 334 for use with optically dense slurries. The slurry fills the space between the two sapphire windows, and the transmission path length through sample cell 162 equals the thickness of spacers 336 and 338. The tapered ramps 312 and 314 are carefully machined into the respective plates 300 and 302 to provide a smooth transition between the input/output lines 168 and 310, and the optical viewing area. This smooth transition prevents slurry agglomeration. Also the inside edges of the sapphire windows have been beveled, as at bevels 344 and 346 to prevent slurry accumulation and agglomeration.

An ultrasonic generator or disrupter 348 is optionally coupled with the sample cell input line 303 for disruption of soft slurry agglomerates. CMP slurry can contain both hard and soft agglomerates, and the soft agglomerates are believed not to scratch semiconductor wafers. The ultrasonic disrupter is used to break up the soft agglomerates before slurry enters the sample cell.

The slurry enters the space defined by spacers 336 and 338 and between windows 326 and 328. Cell 162 is referred to herein as a nonvolumetric sample cell for the reason that some leakage may escape into the cavity 350 surrounding the opening 322, e.g., through non-sealed openings at 352, 354, 356, and 358. This leakage, as well as the flow between windows 326 and 328, is collected by ramp 312 and cell output line 310. The slurry between windows 326 and 328 is exposed to light or electromagnetic radiation from pathways 134 or 136 for particle sensing and analysis by CPU 164 (see FIG. 1).

Figure 4:
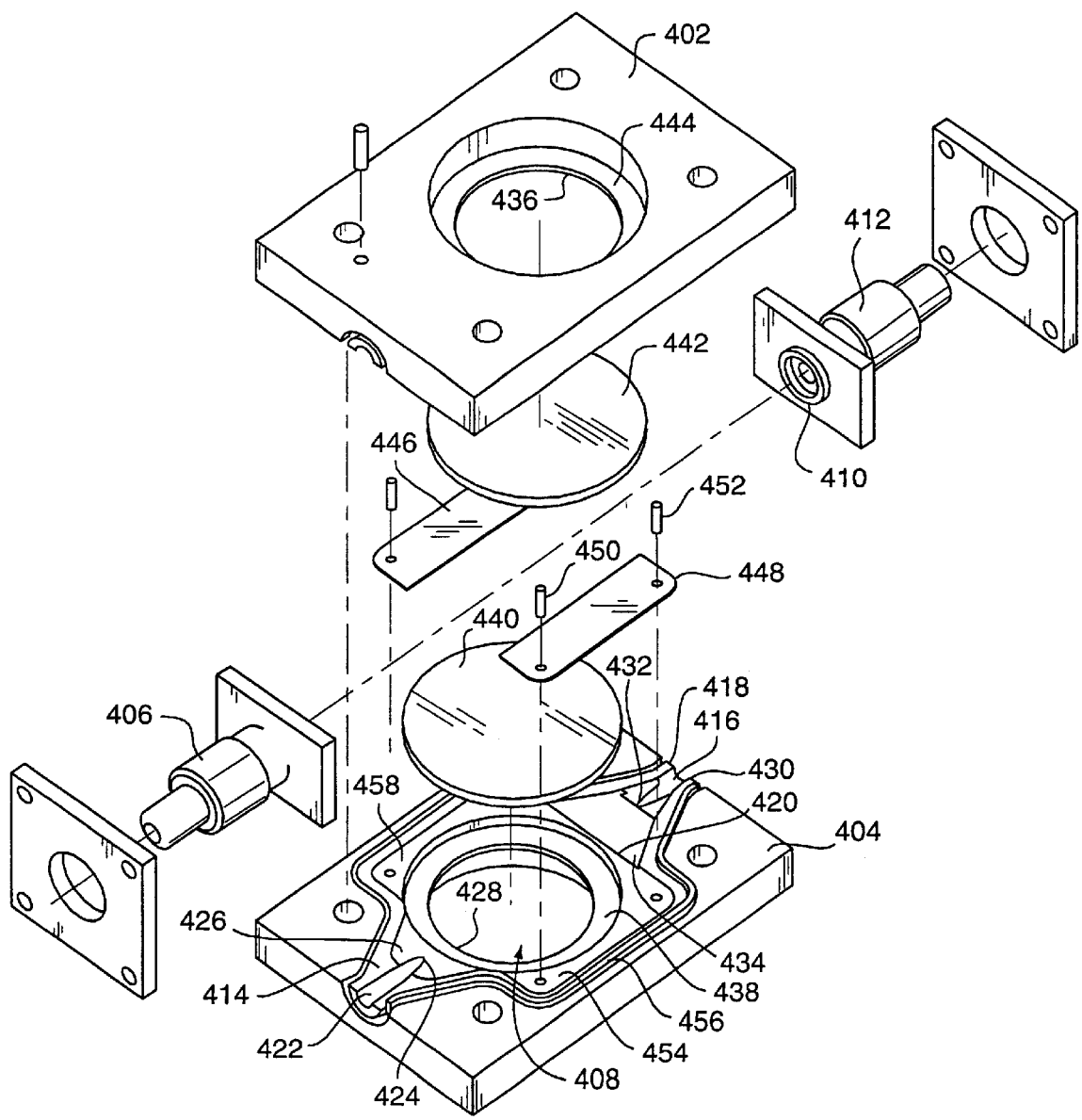
FIG. 4 depicts a second specially constructed sample cell for use in the probe of FIG. 1.

FIG. 4 depicts a second and most preferred volumetric sample cell 400 for use as an alternative to or in combination with the sample cells 162 or 154 of FIG. 3. A housing is formed of top plate 402 and bottom plate 404, which are each machined from a solid, slightly deformable block of chemically resistant material such as TFE Teflon. Sample cell inlet line 406 is connected with an inlet port (not depicted) through which the undiluted CMP slurry from the main CMP slurry line enters the interior space 408 of sample cell 400. Outlet port 410 drains the slurry from space 408 into outlet line 412. Each of top plate 402 and bottom plate 404 are provided with an opposed pair of triangular tapered ramps, e.g., ramps 414 and 416. These ramps are thickest at their respective tips proximate the corresponding port, e.g., tip 418 proximate outlet port 416, and which widen and narrow towards a base remote from the port, e.g., base 420. Ramp 414 contains a conical opening having a maximum volume proximate cell inlet line 406. This volume decreases towards ramp 416 with decreasing volume in the conical opening 422 being equally compensated by increased volume in the portion of ramp 414 surrounding conical opening 422. Conical opening terminates at tip 424 proximate a wedge 426 of increasing narrow width and steepness leading to an interior opening 428. Ramp 416 has a similar conical opening 430 with tip 432 pointing towards ramp 414 and terminating prior to wedge 434.

Each of top and bottom plates 402 and 404 are respectively provided with centrally located circular apertures 428 and 436, which are slightly offset along the fluid flow axis. The interior portions of plates 402 and 404 each contain a first step surrounding the corresponding opening, e.g., first step 438 surrounding opening 428, for receipt of a corresponding sapphire window. For example, a flat sapphire window 440 is received in sealing engagement against step 438. Flat sapphire window 442 identical to window 440 is similarly received in sealing engagement against step 444. A pair of opposed spacers 446 and 448 are retained against flow by corresponding retaining pins, e.g., retaining pins 450 and 452, and fit between the sapphire windows 440 and 442. Each spacer is retained within the confines of a correspondingly sized recess, e.g., as spacer 448 is retained within recess 454. A deformable elastomeric wall 456 sealingly engages top plate 402 and bottom plate 404 to prevent leakage from sample cell 400. The wedges 426 and 434 extend wide enough to meet the spacers 448 and 446. The spacers each sealingly engage both windows 440 and 442. Thus, there is no slurry leakage from the space between windows 440 and 442, i.e., cell 400 is a volumetric cell because it does not leak into the space 458 circumscribing windows 440 and 442.). The optical viewing area between windows 440 and 442 preferably ranges between 50 and 250 microns in thickness for use with optically dense slurries.

Sample cell 400 operates in a similar manner with respect to cell 162, as shown in FIG. 3, though there are volumetric flow differences between the two cells with respect to leakage from the space between the windows. The sapphire windows 440 and 442 together with opposed spacers 446 and 448 define the optical viewing area available to path 134 or 136 (see FIG. 1). The slurry fills the space between the two sapphire windows, and the transmission path length through sample cell 400 equals the thickness of spacers 446 and 448. The tapered ramps 414 and 416 are carefully machined into the corresponding plates 402 and 404 to provide a smooth transition between the input/output lines 406 and 412 relative to the optical viewing area between windows 440 and 442. This smooth transition prevents slurry agglomeration.

The various optical pathways depicted in FIG. 1 comprise a distance along which light may travel. In alternative embodiments, the pathways 114, 116, 120, 124, 126, 134, 140, 142, and 158 may be constructed of optical fibers. In this alternative embodiment, mirrors 152 and 156 are not required. Long pass filters 118, 132, and 160 may be replaced by 1:2 fiber optic couplers. A 1:2 fiber optic coupler may also replace the 50:50 beam splitter 138.

Mie Theory

Measurement of light scattering as a function of angle is also a sensitive measurement technique for CMP slurry particle size distribution. A major disadvantage of this approach is that significant multiple scattering errors appear when the optical depth exceeds 0.1–0.2, where the optical depth is the product of the extinction per unit length times the sample cell thickness. This measurement technique relies upon an unambiguous definition of the scattering angle for each photon. For a doubly scattered photon, the scattering angle for each scattering event is undefined. This limitation necessitates a batch sampling mode of operation, with large amounts of dilution.

By comparison, the spectral transmission measurement technique can operate at optical depths as large as approximately 3.0, allowing one to sample undiluted slurry in a continuous, real time mode, with realistic sample cell dimensions. The spectral transmission measurement technique does not suffer from multiple scattering errors until the diffuse radiation field intercepted by sensor's narrow field of view (typically about 1°), becomes a significant percentage of that remaining in the direct beam.

Optical Model Calculations

Mie scattering gives a complete theoretical description of optical extinction by homogenous spheres. Although particles in all of the CMP slurries are chemically homogeneous, i.e., they are composed of a single known compound, most particles are not spherical. Even so, Mie theory has demonstrated success by modeling the optical extinction of naturally occurring, non-spherical particles, in terms of optically equivalent spheres. Furthermore, extinction is the sum of scattering over all angles plus absorption, and is not as sensitive to particle shape as is the scattering phase function (the angular scattering pattern).

The slurry particle size distribution (PSD) is retrieved from the spectral transmission measurements through utilization of a modified Twomey/Chahine nonlinear inversion algorithm. Equation (1) expresses the measured transmission (T) as a function of wavelength ($\lambda$) in terms of the transmission of sample cell windows ($T_W$), the transmission of the liquid portion of the slurry ($T_L$), and the transmission of the slurry particles ($T_P$).

$$T(\lambda)=T_W(\lambda)T_L(\lambda)T_P(\lambda) \tag{1}$$

By first measuring the transmission of the sample cell filled only with the liquid portion of the slurry, then dividing that into the transmission expressed in Equation (1), one can isolate $T_P(\lambda)$, which is the quantity of interest. Beer's Law is then solved for the particle volume extinction coefficient ($\beta_E(\lambda)$), as shown in Equation (2), where L is the transmission path length or sample cell width. Equation (3) represents the formula for calculating the particle volume extinction coefficient in terms of the particle radius (r), the Mie extinction efficiency ($Q_E$), and the PSD (N(r)), where m is the particle's complex refractive index.

$$\beta_E(\lambda)=-\ln(T_P(\lambda))/L \tag{2}$$

$$\beta_E(\lambda)=\int \pi r^2 Q_E(2\pi r/\lambda,m)N(r)dr \tag{3}$$

Equation (3) must be inverted to solve for the particle size distribution. One class of inversion algorithms is the linear inversion, which provides a less preferred model for reasons that are explained below. The less preferred inversion method transforms the measurement equation into a linear system of equations by replacing the integral with a summation and by representing the collection of equations in the matrix form given by Equation (4). In this latter equation, elements of matrix $\underline{Q}$ consist of $\pi r^2 Q_E$. The $\underline{Q}$ matrix has m rows, one for each wavelength, and n columns, one for each radius; m must be greater than or equal to n. The $\underline{N}$ matrix is n by 1, and the elements consist of the particle size distribution. The $\underline{\beta}$ matrix is m by 1, and the elements consist of the measured spectral volume extinction coefficients.

$$\underline{Q}_{\square R}\underline{N}_R=\underline{\beta}_{80} \tag{4}$$

Equation (4) can be formally inverted to solve for the particle size distribution, utilizing conventional inversion algorithms which constrain the solution to various conditions, such as smoothing (minimize the first or second derivative), or minimize the departure from a first guess, according to Twomey, "Comparison of constrained linear inversion and an iterative nonlinear algorithm applied to the indirect estimation of particle size distributions", J. comp. Phys., Vol. 18, No. 2, pp. 188–200 (1975), which is hereby incorporated by reference to the same extent as though fully disclosed herein.

Constraints are required in all inversion algorithms because the existence of measurement error and quadrature error (replacing the integral with a sum) result in the fact that a family of particle size distributions will satisfy the measurement equation. For any inversion method, the uncertainty in the retrieved solution can be reduced by: (a) choosing a more sensitive measurement technique, (b) reducing the measurement error, (c) increasing the number of measurements, which reduces the effects of quadrature error.

Linear inversion techniques are computationally efficient, but they are a poor choice for the CMP slurry problem because the most popular constraint, i.e., that of smoothing, is a poor choice for slurry particle size distributions. These distributions are not necessarily smooth or continuous. Additionally, linear inversion algorithms can be unstable to an extent that produces physically unrealistic answers.

The CMP slurry measurement problem consists of detecting departures from the normal or specified particle size distribution, which makes a non-linear, iterative, inversion algorithm a natural choice and a more preferred model for use in practicing the invention. With the iterative approach, one can start with the normal particle size distribution as a first guess. The iterative calculations converge toward a final solution in an orderly fashion, where convergence is based upon a difference between the measured spectral extinction and that calculated from the last guess particle size distribution. Alternatively, one can start with a delta function as a first guess. Iteration is halted when this difference becomes less than some predetermined error bound. This preferred method of inverting equation (4) is based on previous work in the field of atmospheric remote sensing by Cerni, "Aircraft-based remote sensing or tropospheric profiles for meoscale studies", Advances in Remote Sensing Retrievals, pp. 339–347 A. Deepak Publ., Hampton, Va. (1985); and Chahine, "Inverse problems in radiative transfer: Determination of atmospheric parameters", J. Atmos. Sci., Vol. 27, pp 960–967 (1970) and Twomey (1975, referenced earlier), which are incorporated by reference herein to the same extent as though fully disclosed herein.

The algorithm given in Equations (5) and (6) is a preferred means of inverting the spectral transmission data to retrieve the particle size distribution. The superscripts I and I-1 refer to successive numbers of iterations. The subscripts P refer to different wavelengths, and indicate that all the measurements are utilized in adjusting the particle size distribution at a single r value. Additionally, one can improve the accuracy of the retrieval by adding conservation of mass (slurry percent solids by weight), and summing Equation (5) over all wavelengths.

$$N_P^{(I)}(r)=[1+(r_P^{(I-1)}-1)\pi r^2 Q_E(2\pi r/\lambda,m)]N_P^{(I-1)}(r) \tag{5}$$

$$r_P^{(I-1)}=\beta_E(\lambda)/[\int \pi r^2 Q_E(2\pi r/\lambda,m)N_P^{(I-1)}(r)dr] \tag{6}$$

EXAMPLE 1

VERIFICATION OF THE MODEL WITH EXPERIMENTAL RESULTS

The Mie theory optical model results were verified with the use of an Acton SP-305 spectrometer system retrofitted with a sample cell according to FIG. 3. The sample cell was constructed to provide sapphire windows having a 40 mm diameter with the windows being held approximately 100 microns apart in a PVDF chemically resistant block. The detector module utilized one Si and one InGaAs photodiode to cover the broad 0.20–2.5 micron spectral range.

Figure 5:
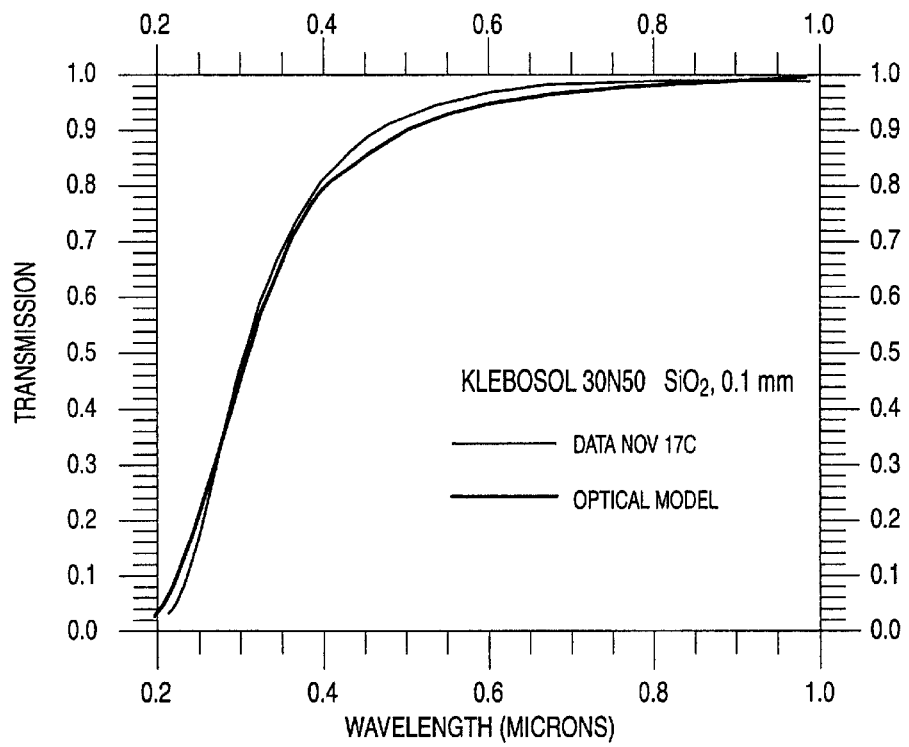
FIG. 5 depicts a comparison between calculation data from an optical model according to the present invention and spectral transmission data obtained from a manufacturer's CMP slurry.
Figure 6:
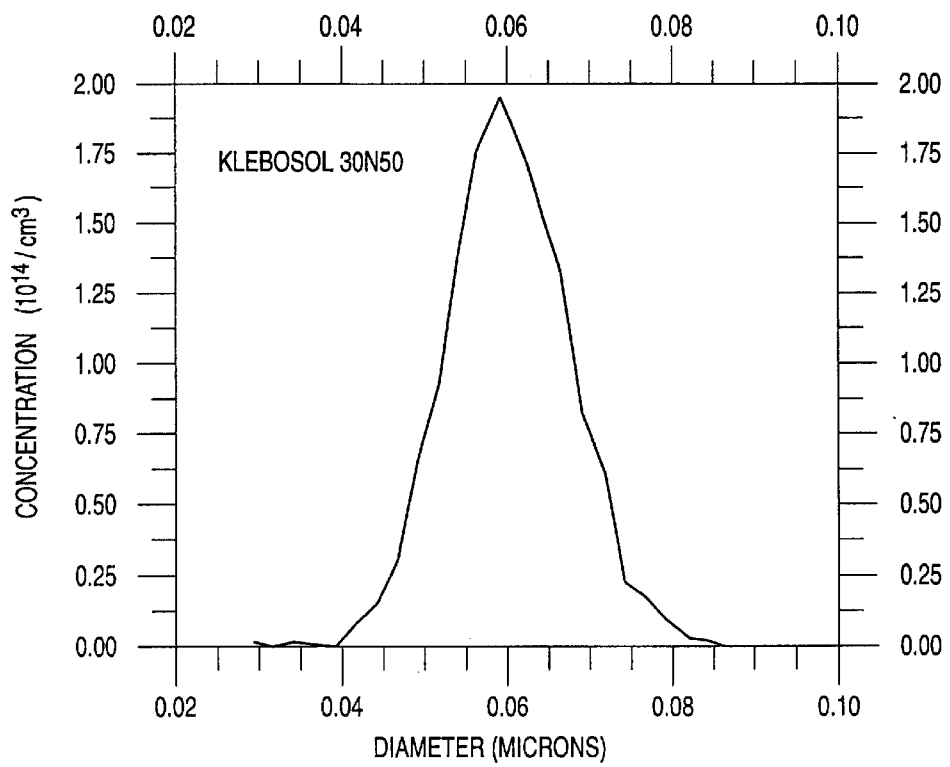
FIG. 6 depicts a manufacturer's scanning electron microscope-based particle size distribution corresponding to the spectral transmission data of FIG. 5.

FIG. 5 shows a comparison between optical model predictions and experimental data for Solution Technology Klebosol 30N50 oxide slurry, which consists of $SiO_2$ particles immersed in a weak $NH_4OH$ solution with a pH of 10.9. The product as tested contained 30% solids by weight, which is the basic product produced by Solution Technology. The product it is typically diluted to 18% solids by weight just prior to use in CMP wafer planarization. Thus, the tested product was even more optically dense than an actual CMP slurry using the product. As an input, the optical model utilized a particle size distribution provided by Solution Technology, shown in FIG. 6, which the manufacturer purports to have been measured with an electron microscope. The comparison shown in FIG. 5 demonstrates a remarkably good agreement between measured transmission data and optical model predictions.

Possible reasons for the observed small differences between the two curves (theoretical and actual results) of FIG. 5 include: (1) departure of the optical behavior of this unusually dense particulate suspension from that predicted by Mie theory, (2) departures of the sample particle size distribution from the typical particle size distribution provided by the slurry manufacturer, (3) errors in the particle size distribution measurements provided by the slurry manufacturer, due to the poor sample statistics provided by analysis of electron microscope imagery, (4) unexpected slurry liquid absorption bands, and (5) errors in the experimental spectral transmission measurement technique. The combined effects of these error sources are minor in this example. Klebosol 30N50 is described by the manufacturer as consisting of individual spheres, which are grown from seed in a saturated $SiO_2$ solution. As such, one would expect accurate predictions from Mie theory.

The experimental data shown in FIG. 5 was truncated at a transmission value of 0.030, below which the measured data indicated a leveling off and then an increase in transmission as wavelength decreased and optical depth increased. Such a result is unphysical, and indicates that the multiply scattered radiation, which is scattered in a near forward direction, has become comparable to or greater than the transmitted radiation. This result is expected to occur at some point with increasing optical depth and with a finite instrument field of view. The detector system used the SP-305 spectrometer, which is designed to have a nominal 1° field of view, and this scattering effect was predicted to be observed at a transmission value of approximately 0.050, i.e., an optical depth of 3.

EXAMPLE 2

VERIFICATION OF THE MODEL WITH EXPERIMENTAL RESULTS

Figure 7:
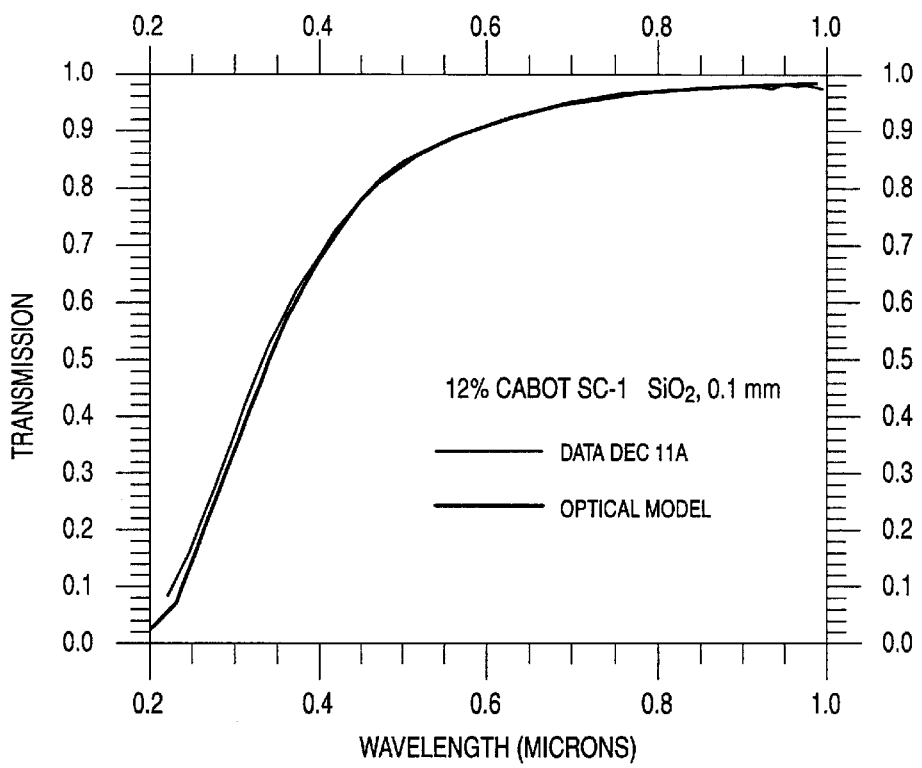
FIG. 7 depicts a comparison between calculation data from an optical model according to the present invention and spectral transmission data obtained from a manufacturer's CMP slurry.
Figure 8:
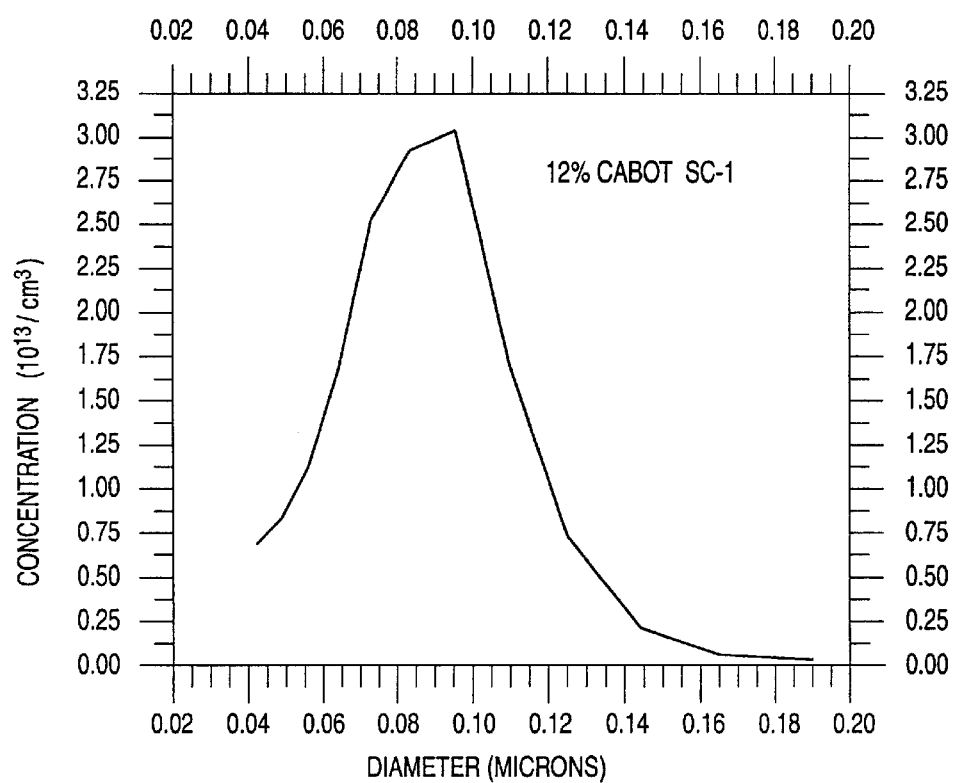
FIG. 8 depicts reported data for a particle size distribution corresponding to the spectral transmission data of FIG. 7.

FIG. 7 shows optical model predictions and experimental data for Cabot SC-1 oxide slurry, which consists of $SiO_2$ particles immersed in a weak KOH solution having a pH of 10.3. This sample was diluted to 12% solids by weight, which is the concentration at which it is used for CMP wafer planarization. The particle size distribution used as input to the optical model is plotted in FIG. 8, and represents a modified version of the Cabot SC-1 PSD measured by Bare and Lemke: "Monitoring slurry stability to reduce process variability", Micro. Vol. 15, No. 8, pp. 53–63 (1997) (the BH97 particle size distribution) using an Horiba LA-910 light scattering particle size distribution probe. A modification to the BH97 particle size distribution consisted of multiplying each particle size distribution size bin by 0.56. The 0.56 factor was chosen to obtain good fit to the measured transmission data.

Figure 9:
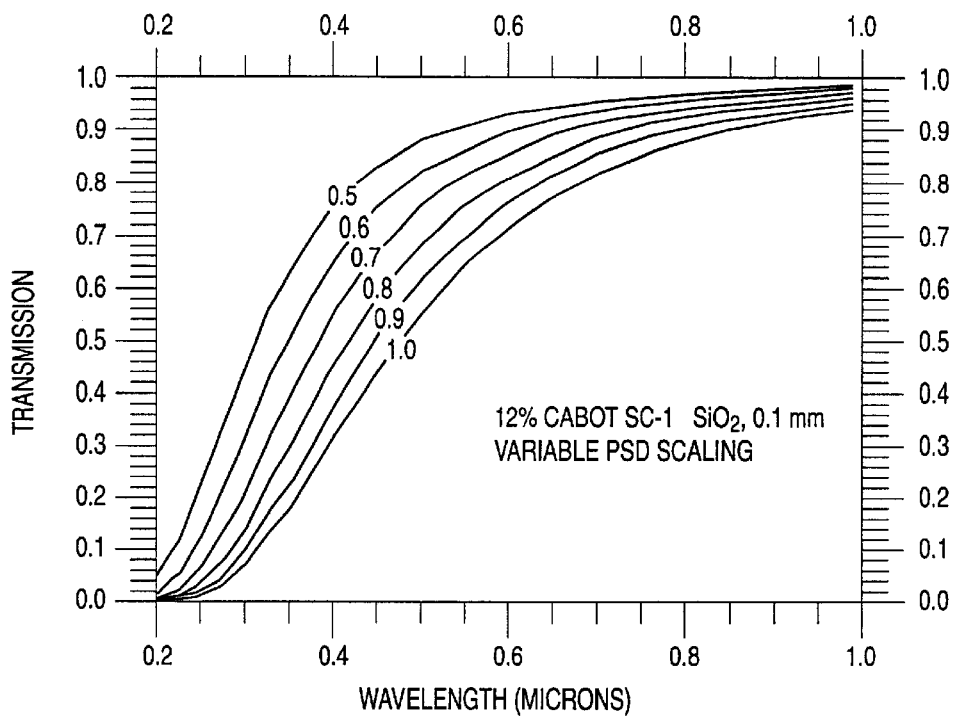
FIG. 9 depicts the calculated spectral transmission data effects of varying a distribution size bin factor to adjust the particle size distribution data shown in FIG. 10.
Figure 10:
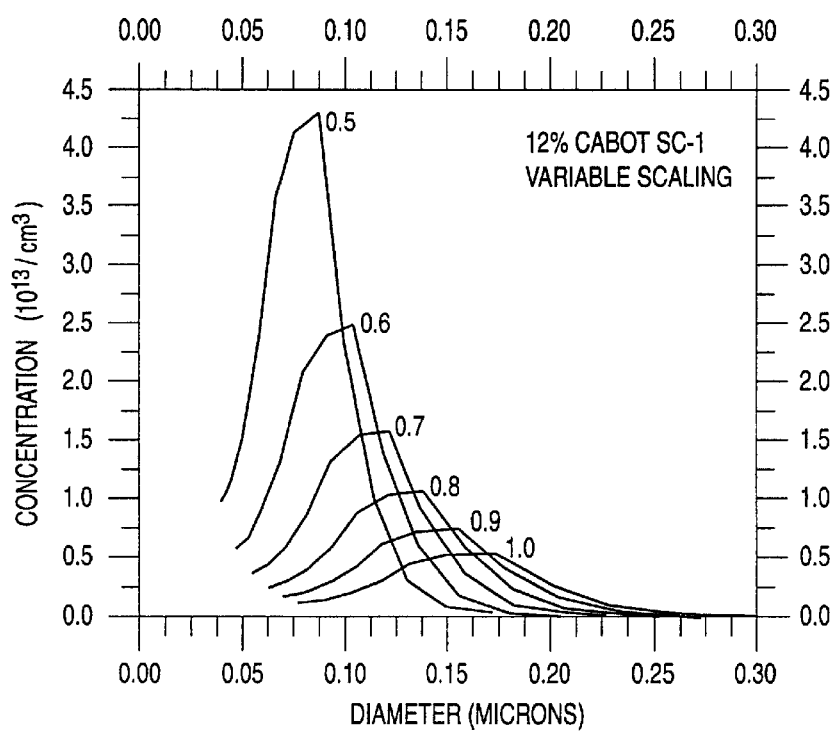
FIG. 10 depicts the calculated concentration data effects of varying a distribution size bin.

FIGS. 9 and 10 show how changes in this distribution size bin factor affect the transmission spectrum, and serve as another indication of the sensitivity of the spectral transmission measurement technique. Cabot SC-1 is a fumed silica product produced by combining reactant gases in a flame, and is known to consist of chains of tiny spheres fused together. Hence, the diameter of such a particle chain is not well defined. The extinction cannot be accurately modeled by Mie theory, and one should expect differences in the particle size distribution obtained by different measurement techniques. Given this uncertainty, a factor of 0.56 is reasonable.

In FIG. 9, the measured spectrum was truncated at a transmission value of 0.079, due to apparent errors introduced by multiple scattering. This higher value of transmission cut-off for SC-1 versus 30N50 (0.079 versus 0.030), is consistent with the larger particles present in the former slurry, which is known to produce more forward scattering. It is also consistent with more forward scattering produced by non-spherical versus spherical particles.

FIG. 11 depicts a schematic process diagram of process P1100 for use in operating the probe shown in FIG. 1. In step P1102, optically dense CMP slurry is diverted from the main slurry line to the sample cells 154 and 162. In step P1104; the flow of slurry is narrowed through the sample cells to provide an optical depth that permits meaningful spectral transmission data. Light is transmitted through the narrowed slurry along pathways 134 and 136 in step P1106. Pathways 140 and 142 deliver this light to the spectrophotometers 128 and 130 in step P1108. The spectrophotometers produce signals representative of the detected light and particles in the cells 154 and 162. These signals are transmitted to CPU 164 for processing according to the modified Twomey/Chahine technique according to equations 1–6.

At the conclusion of step P1108, step P1110 includes the detection of light transmitted along pathway 126 to spectrophotometers 128 and 130 due to the rotation of chopper blade 122 and the reflective action of mirror 202. The detector counts are transmitted to CPU 164 for registration of source lighting conditions without particle scattering from sample cells 154 and 162.

In step P1112, the detector background count is measured with chopper blade 122 positioned to place solid disk 204 in path 120 for blocking the transmission of light along either path 126 or 134. Spectrophotometers 128 and 130 again produce signals corresponding to detected light, and these signals are transmitted to CPU 164 which interprets the signals as background count information that can be subtracted from total counts received from light traveling along pathways 126 or 134.

In step P1114, CPU 164 uses stored detector signals from steps P1108, P1110, and P1112 to calculate, display and store a particle size distribution, as discussed above. Steps P1106–1114 are continuously repeated to perform real time measurements of the particle size distribution in the CMP slurry.

Those skilled in the art will understand that the preferred embodiments described above may be subjected to apparent modifications without departing from the true scope and spirit of the invention. The inventors, accordingly, hereby state their intention to rely upon the Doctrine of Equivalents, in order to protect their full rights in the invention.

What is claimed is:

1. A particle size distribution probe for measuring the particle size distribution of optically dense slurries, said probe comprising:

at least one light source capable of emitting a plurality of wavelengths;

at least one detector element sensitive to wavelengths emitted by said light source;

at least one sample cell having optical qualities permitting particle size measurements to be performed at wavelengths corresponding to sensitivity of said detector element;

means for transmitting light from said light source through said sample cell and then to said detector to obtain detector signals for a particle size distribution measurement; and means for processing detector signals from said detector to obtain a particle size distribution measurement, wherein said sample cell includes means for reducing an optical depth in a flowing optically dense slurry to permit particle size distribution measurements without substantial dilution or agglomeration of said slurry.

2. The probe as set forth in claim 1 wherein said reducing means in said sample cell includes means for reducing said optical depth to less than 3, where said optical depth is the product of an extinction per unit length in said slurry times a thickness of said slurry in an optical path through said sample cell.

3. The probe as set forth in claim 2 wherein said reducing means in said sample cell includes means for reducing an optical path through said sample cell to a length ranging from 50 to 250 microns.

4. The probe as set forth in claim 1 wherein said means for transmitting light and said means for processing detector signals are operably configured to provide continuous on-line sampling for real time process control information including said particle size distribution measurement.

5. The probe as set forth in claim 1 wherein said reducing means includes a first window and a second window spaced apart to provide said optical depth.

6. The probe as set forth in claim 5 wherein said first window and said second window are sapphire windows.

7. The probe as set forth in claim 1 wherein said reducing means further includes a tapered ramp and an inlet port, said tapered ramp narrowing from said inlet port towards said first window and said second window, said tapered ramp widening as it narrows.

8. The probe as set forth in claim 1 wherein said means for processing detector signals includes processing of detector signals representative of extinction through said sample cell as a function of wavelength.

9. The probe as set forth in claim 1 wherein said probe is operably configured to perform particle size distribution measurements on CMP slurry as said optically dense slurry without any dilution of said CMP slurry.

10. The probe as set forth in claim 9 including means for supplying a sample portion of CMP slurry from a main process supply to said probe for particle size distribution measurements by said probe and for returning said sample portion of CMP slurry from said probe to said main process supply after said probe has performed said particle size distribution measurements.

11. The probe as set forth in claim 1 including means, positioned relative to said light transmitting means, for chopping light traveling between said light source and said sample cell.

12. The probe as set forth in claim 11 wherein said light chopping means provides means for transmitting light to said sample cell and means for blocking transmission of light to said sample cell.

13. The probe as set forth in claim 12 wherein said light blocking means includes means for transmitting light to said detector without passage of said light through said sample cell.

14. The probe as set forth in claim 1 wherein said light blocking means further includes means for blocking passage of light to said detector.

15. The probe as set forth in claim 14 wherein said processing means includes means for calibrating said probe through use of detector signals obtained when said light blocking means is transmitting light from said light source to said detector without passage of said light from said light source through said sample cell.

16. The probe as set forth in claim 15 wherein said processing means includes means for calibrating said probe through use of detector signals obtained when said light blocking means is blocking passage of light from said light source to said detector.

17. The probe as set forth in claim 16 wherein said processing means includes a chopper blade having a mirror providing means for measuring the time and the temperature drift of said source, and a solid region providing means for measuring time and temperature drift of said detector element, said mirror and said solid region permitting autonomous operation in an industrial environment with reduction in need to take said probe off line for frequent measurement of reference spectra.

18. The probe as set forth in claim 1 wherein said processing means includes means for using a modified Twomey/Chahine-based nonlinear iterative conversion to obtain a particle size distribution measurement.

19. The probe as set forth in claim 1 wherein said detector element includes a plurality of fixed grating spectrometers each having a corresponding detector array, to accomplish continuous wavelength coverage over the spectral range of interest, and to provide simultaneous spectral transmission measurements at one thousand to several thousand wavelengths.

20. The probe as set forth in claim 1 wherein said light source includes a deuterium source for ultraviolet radiation and a quartz tungsten halogen source for visible and infrared radiation.

21. The probe as set forth in claim 1 wherein said detector provides means for detecting radiation from said transmitting means at spectral wavelengths ranging from 0.20 to 2.5 microns.

22. The probe as set forth in claim 1 including means for using ultrasound to disrupt optically dense slurry just prior to entry of said optically dense slurry into said sample cell.

23. The probe as set forth in claim 1 wherein said at least one sample cell includes a plurality of sample cells each tuned to a specific wavelength range wherein transmission through said cell is maintained in a range between about 0.10 to 0.90.

24. A method of obtaining particle size distribution measurements from optically dense slurries, comprising the steps of:

diverting a portion of optically dense slurry from a main slurry line;

introducing said optically dense slurry into a sample cell in substantially undiluted form;

narrowing flow of said optically dense slurry within said sample cell to reduce an optical depth through said optically dense slurry and to permit particle size distribution measurements without dilution of said slurry;

transmitting light through said optically dense slurry in said sample cell;

detecting the light transmitted through said optically dense slurry in said sample cell with production of corresponding detector signals; and calculating a particle size distribution through use of said detector signals.

25. The method as set forth in claim 24 wherein said step of narrowing flow within said sample cell includes reducing said optical depth to less than 3, where said optical depth is the product of an extinction per unit length in said slurry times a thickness of said slurry in an optical path through said sample cell.

26. The method as set forth in claim 24 wherein said step of transmitting light includes transmitting of a plurality of wavelengths of light, and said step of detecting comprises the production of detector signals representative of extinction through said sample cell as a function of wavelength.

27. The method as set forth in claim 24 wherein said step of narrowing flow within said sample cell includes reducing an optical path through said sample cell to a length ranging from 50–250 microns.

28. The method as set forth in claim 24 wherein said step of narrowing flow within said sample cell includes widening said flow as said flow narrows.

29. The probe as set forth in claim 24 including a step of returning said portion of optically dense slurry to said main slurry line.

30. The method as set forth in claim 24 wherein step of transmitting light includes transmitting light through use of a plurality of diffraction gratings all in fixed configuration, dispersing radiation onto a plurality of detector arrays to accomplish continuous wavelength coverage over the spectral range of interest, and said calculating step includes providing simultaneous spectral transmission measurements at one to several thousand wavelengths.

31. The method as set forth in claim 24 including a step of chopping light traveling between said light source and said sample cell.

32. The method as set forth in claim 31 wherein said light chopping step includes diverting light from said sample cell while measuring the time and temperature drift of a spectral source, and while measuring time and temperature drift of a detector element, said diverting step permitting autonomous calibration in an industrial environment with reduction in need to take said probe off line for frequent measurement of reference spectra.

33. The method as set forth in claim 32 wherein said light chopping step includes transmitting light to said detector without passage of said light through said sample cell.

34. The method as set forth in claim 32 wherein said light chopping step further includes blocking of light to said detector.

35. The method as set forth in claim 34 wherein said step of calculating a particle size distribution includes calibrating said probe through use of detector signals obtained concurrently with said light blocking step.

36. The method as set forth in claim 24 wherein said step of calculating a particle size distribution comprises using a modified Twomey/Chahine-based nonlinear iterative conversion to obtain a particle size distribution measurement.

37. The method as set forth in claim 24 wherein said step of detecting includes detecting radiation consisting of spectral wavelengths ranging from 0.20 to 2.50 microns.

38. The probe as set forth in claim 24 including a step of using ultrasound to disrupt optically dense slurry just prior to entry of said optically dense slurry into said sample cell.

39. In a sample cell having windows for the transmission of light and an interior flow space permitting continuous flow of slurry, the improvement comprising: an enclosed flow channel for reducing the optical depth in said interior flow space to facilitate transmission of light through an optically dense slurry in said interior flow space while maintaining substantially laminar flow through said flow space without particle agglomeration from said optically dense slurry and without dilution of said slurry.

40. A particle size distribution probe for measuring the particle size distribution of chemical mechanical polishing (CMP) slurries, said probe comprising:

a radiation source providing electromagnetic radiation;

a sample cell system for permitting said radiation to be transmitted through undiluted CMP slurry as used in a semiconductor manufacturing process while it flows through said cell;

a radiation detector responsive to said transmitted radiation and producing a detector signal; and a processor responsive to said detector signal and producing an output signal representative of said particle size distribution.

41. A probe as in claim 40 and further including a source reference optical system for measuring a condition of said radiation source.

42. A probe as in claim 41 wherein said condition includes the time and temperature drift of said radiation source.

43. A probe as in claim 40 and further including a background reference optical system for measuring a condition of said radiation detector.

44. A probe as in claim 43 wherein said condition includes the time and temperature drift of said radiation detector.

45. A probe as in claim 40 including two of said sample cells, each having a different slurry thickness through which said radiation is transmitted.

46. A particle size distribution probe for measuring the particle size distribution of chemical mechanical polishing (CMP) slurries, said probe comprising:

a radiation source providing electromagnetic radiation;

a sample cell system for permitting said radiation to be transmitted through said CMP slurry while it flows through said cell;

a detector responsive to said transmitted radiation and producing a detector signal; and a processor responsive to said detector signal and producing an output signal representative of said particle size distribution; wherein said sample cell system comprises: a sample cell inlet connector of a suitable size for connection to a CMP slurry line of a semiconductor manufacturing facility; an optical viewing area having a thickness sufficiently small that a sufficient amount of said radiation will be transmitted through undiluted CMP slurry filling said viewing area to provide said output signal; a sample cell outlet connector of a suitable size for connection to a CMP slurry line of a semiconductor manufacturing facility; an inlet tapered ramp connecting said inlet connector and said optical viewing area; an outlet tapered ramp connecting said optical viewing area and said outlet connector.

47. A probe as in claim 46 wherein said optical viewing area has a thickness in the range of 50 microns to 250 microns.

48. A probe as in claim 46 including two of said sample cells, each having a different slurry thickness through which said radiation is transmitted.

* * * * *